United States Patent

Cavalla et al.

[11] Patent Number: 6,040,447
[45] Date of Patent: Mar. 21, 2000

[54] PURINE COMPOUNDS HAVING PDE IV INHIBITORY ACTIVITY AND METHODS OF SYNTHESIS

[75] Inventors: David J. Cavalla, Cambridge, United Kingdom; Mark Chasin, Manalapan, N.J.; Peter Hofer, Liestal, Switzerland

[73] Assignee: Euro-Celtique S.A., Luxembourg

[21] Appl. No.: 09/209,922

[22] Filed: Dec. 10, 1998

Related U.S. Application Data

[60] Provisional application No. 60/069,371, Dec. 12, 1997.

[51] Int. Cl.⁷ .................. C07D 473/34; C07D 239/48; C07D 239/42
[52] U.S. Cl. .................. 544/277; 544/322; 544/329
[58] Field of Search .................................. 544/277

[56] References Cited

PUBLICATIONS

Montgomery, J. Med Chem 15, 1189, 1972.

(List continued on next page.)

*Primary Examiner*—Mark L. Berch
*Attorney, Agent, or Firm*—Davidson, Davidson & Kappel, LLC

[57] ABSTRACT

The present invention comprises a method of synthesizing compounds having the formula (I):

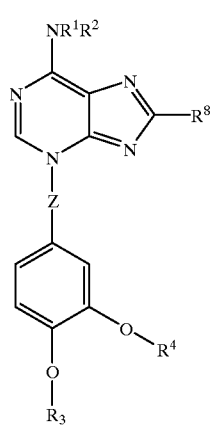

(I)

wherein:

$Z, R^1, R^2, R^3, R^4$ and $R^8$ are defined herein, which comprises the steps of (a) reacting a compound of the formula (II)

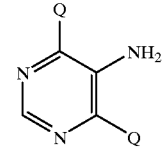

(II)

wherein Q is a halogen, with an effective amount of a compound selected from the group consisting of an acid anhydride or an acid halide; to form a compound of the formula (III)

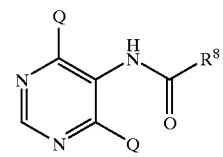

(III)

b) transforming the 6-halo group of said compound (III) to an amine by displacement with ammonia to form compound (IV)

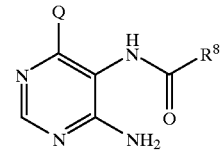

(IV)

(c) reacting said compound (IV) with a base to cause cyclization to a 6-halo intermediate, said 6-halo group is then transformed to an amine by displacement with an amine to form compound (V)

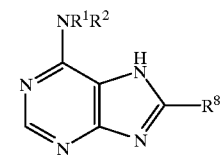

(V)

(d) reacting said compound (V) with an effective amount of compound (VI)

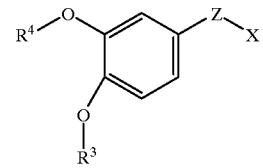

(VI)

wherein X is a halogen; to form the compound of formula (I).

12 Claims, No Drawings

OTHER PUBLICATIONS

Some New N–Methylpurines, Gertrude B. Elion, CIBA foundation Symp. Chem Biol. Purines, 1957, pp. 39–49.

Selective Type IV Phosphodiesterase Inhibitors as Antiasthmatic Agents. The Syntheses and Biological Activities of 3–(Cyclopentyloxy)–4–methoxybenzamides and Analogues, Michael J. Ashton, et al., Journal of Medicinal Chemistry, 1994, vol. 37, No. 11, pp. 1696–1703.

Synthesis of 3–Methylisoguanine [6–Amino–3–methylpurin–2(3H)–one], G.T. Rogers and T.L.B. Ulbricht, J. Chemical Soc.(C), 1971, pp. 2364–2366.

Synthesis of Potential Anticancer Agents. XIX. 2–Substituted $N^6$–Alkyladenines, John A. Montgomery. Lee B. Holum and Thomas P. Johnston. The Kettering–Meyer Laboratory, Southern Research Institute, Aug. 5, 1959, vol. S. pp. 3963–3967.

N–Alkyl Derivatives of Purine–6(1H)–thione, John A. Montgomery, et al., Journal of Medicinal Chemistry, 1972, vol. 15, No. 11, pp. 1189–1192.

PURINE COMPOUNDS HAVING PDE IV INHIBITORY ACTIVITY AND METHODS OF SYNTHESIS

This application is a continuation-in-part of provisional application Ser. No. 60/069,371, filed Dec. 12, 1997.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

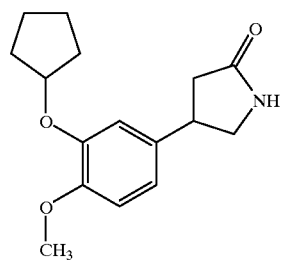

and of RO-20-1724, which has the following structural formula (B):

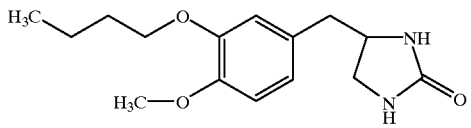

have been studied.

U.S. Pat. No. 4,308,278 discloses compounds of the formula (C)

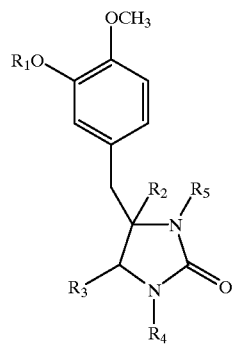

wherein $R_1$ is ($C_3$–$C_6$) cycloallyl or benzyl; each of $R_2$ and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

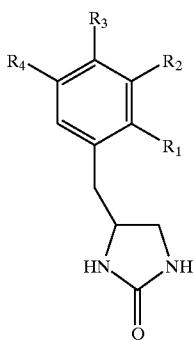

Substituents $R_1$–$R_4$ in Formula D represent a variety of groups, including hydrogen and lower alkyl.

PCT publication WO 87/06576 discloses antidepressants of Formula E:

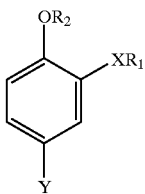

wherein $R_1$ is a polycycloalkyl group having from 7 to 11 carbon atoms; $R_2$ is methyl or ethyl; X is O or NH; and Y comprises a mono-or bicyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia, including vascular dementia, multi-in-farct dementia and Alzheimer's Disease, and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent.

The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

OBJECTS AND SUMMARY OF THE INVENTION

It is accordingly a primary object of the present invention to provide new compounds which are more effective selective PDE IV inhibitors than known prior art compounds.

It is another object of the present invention to provide new compounds which act as effective PDE IV inhibitors with lower PDE III inhibition.

It is another object of the present invention to provide methods for treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

It is another object of the present invention to provide a method for treating a patient suffering from disease states such as asthma, allergies, inflammation, depression, dementia, including vascular dementia, multi-in-farct dementia, and Alzheimer's Disease, a disease caused by Human Immunodeficiency Virus and disease states associated with abnormally high physiological levels of inflammatory cytokines.

Other objects and advantages of the present invention will become apparent from the following detailed description thereof.

With the above and other objects in view, the present invention comprises compounds having the general formula (I):

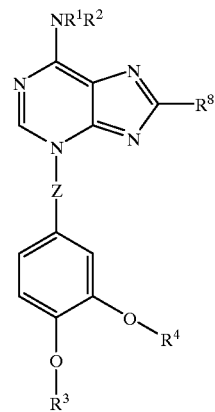

wherein:
Z is selected from the group consisting of alkylene groups such as $CH_2$, $CH_2CH_2$, $CH(CH_3)$; alkenylene groups such as CH=CH; alkynylene groups such as C≡C; and NH, N($C_1$–$C_3$ alkyl), O, S, C(O)$CH_2$ and $OCH_2$;

$R^1$ and $R^2$ are independently selected from the group consisting of hydrogen and a $C_1$–$C_8$ straight or branched alkyl or $C_3$–$C_8$ cycloalkyl;

$R^3$ is a $C_1$–$C_{12}$ straight or branched alkyl;

$R^4$ is a $C_3$–$C_{10}$ cycloalkyl optionally substituted with OH, or a $C_3$–$C_{10}$ cycloalkenyl optionally substituted with OH, and $R^8$ is a $C_1$–$C_8$ straight or branched alkyl or a $C_3$–$C_8$ cycloalkyl, optionally substituted with OH.

The present invention is also related to methods of using compounds of formula (I) for treating patients who can benefit from a modification of PDE IV enzyme activities in their bodies.

The invention also comprises methods of making compounds of formula (I), according to a four step synthetic scheme as generally set forth in Scheme 1. The stated conditions in Scheme 1 are includes as examples only, and are not meant to be limiting in any manner.

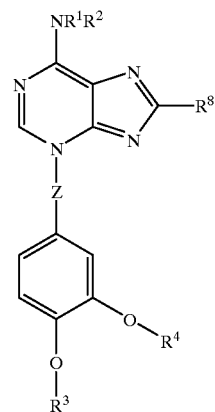
(I)

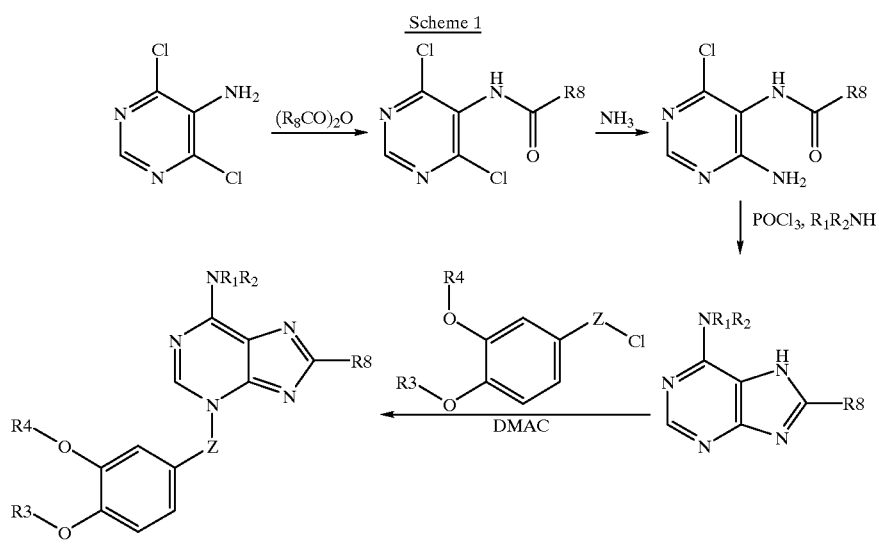
Scheme 1

The invention is also related to a method of treating mammals with the above compounds.

DETAILED DESCRIPTION OF THE INVENTION

The present invention is directed to compounds having the general formula (I):

wherein:

Z is selected from the group consisting of alkylene groups such as $CH_2$, $CH_2CH_2$, CH($CH_3$), alkenylene groups such as CH=CH; alkynylene groups such as C≡C; and NH, N($C_1$–$C_3$ alkyl), O, S, C(O)$CH_2$ and $OCH_2$;

$R^1$ and $R^2$ are independently selected from the group consisting of hydrogen and a $C_1$–$C_8$ straight or branched alkyl or $C_3$–$C_8$ cycloalkyl;

$R^3$ is a $C_1$–$C_{12}$ straight or branched alkyl;

$R^4$ is a $C_3$–$C_{10}$ cycloalkyl optionally substituted with OH, or a $C_3$–$C_{10}$ cylcoalkenyl optionally substituted with OH; and $R^8$ is a $C_1$–$C_8$ straight or branched alkyl or a $C_3$–$C_8$ cycloalkyl optionally substituted with OH.

As used herein, the following terms are intended to have the meaning as understood by persons of ordinary skill in the art, and are specifically intended to include the meanings set forth below:

"Alkyl" means a linear or branched aliphatic hydrocarbon group having a single radical. Examples of alkyl groups include methyl, propyl, isopropyl, butyl, n-butyl, isobutyl, sec-butyl, tert-butyl, pentyl, hexyl, heptyl, cetyl, and the like. A branched alkyl means that one or more alkyl groups such as methyl, ethyl or propyl are attached to a linear alkyl chain.

The term "cycloalkyl" means a non-aromatic mono- or multicyclic ring system having a single radical. Exemplary monocyclic cycloalkyl rings include cyclopentyl cyclohexyl and cycloheptyl. Exemplary multicylic cycloalkyl rings include adamantyl and norbornyl.

The term "cycloalkenyl" means a non-aromatic monocyclic or multicyclic ring system containing a carbon-carbon double bond and having a single radical. Exemplary monocyclic cycloalkenyl rings include cyclopentenyl, cyclohexenyl or cycloheptenyl. An exemplary multicyclic cycloalkenyl ring is norbornenyl. "Alkylene" means a linear or branched aliphatic hydrocarbon group having two radicals. Examples of alkylene groups include methylene, propylene, isopropylene, butylene, and the like.

The term "alkenylene" means a linear or branched aliphatic hydrocarbon group containing a carbon-carbon double bond, having two radicals.

The term "alkynylene" means a linear or branched aliphatic hydrocarbon group containing a carbon-carbon triple bond and, having two radicals.

"Alkoxy" means an alkyl-O-group in which the alkyl group is as previously described Exemplary alkoxy groups include methoxy, ethoxy, n-propoxy, i-propoxy, n-butoxy and heptoxy.

The term "cycloalkoxy" means a cycloalkyl-O-group in which the cycloakyl group is as previously described. Exemplary cycloalkoxy groups include cyclopentyloxy.

As used herein, the term "patient" includes both human and other mammals.

The present invention also includes organic and inorganic salts, hydrates, esters, prodrugs and metabolites of the compounds of formula I.

The compounds of the present invention can be administered to anyone requiring PDE IV inhibitor. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solutions and suspensions. The compounds of the present invention can be administered alone or can be combined with various pharmaceutically acceptable carriers and excipients known to those skilled in the art, including but not limited to diluents, suspending agents, solubilizers, binders, retardants, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from no-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal track. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients,* American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems,* (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

DETAILED DESCRIPTION OF THE PREFERRED EMBODIMENT

As used herein, the term "Et" refers to any ethyl group, and the term "Bu" refers to a butyl group. "Bu" refers to a tertiary butyl group. The term "THF" refers to tetrohydrofuran. The term "DMAC" refers to dimethyl acetate. The term "Ph" refers to a phenyl group. The terms Z; $R^1$; $R^2$; $R^3$; $R^4$; and $R^8$ refer to the terms as defined in this application.

The synthetic pathway described in Scheme 1 for producing xanthine compounds of FIG. I is described as follows:

In step (a) of the synthetic scheme, a pyrimidine compound (II) wherein Q is a halide, preferably chloride, is reacted with an acid e.g. an acid chloride such as isobutyrylchloride, or an acid anhydride, to form compound (III), as depicted below:

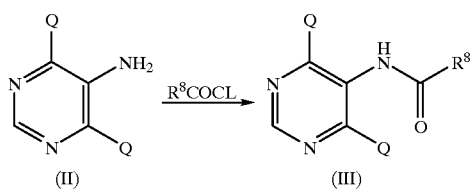

The acid reaction preferably occurs from about 50° C. to about 150° C., although other temperatures ranges can be used if necessary. This reaction may occur in the presence of a suitable solvent e.g. acetonitrile ($CH_3CN$), DMF or a combination thereof.

Step (b) of the synthetic scheme involves the 6-halo group of compound (III) being transformed to the amine by displacement to give compound (IV) of the invention, for example as shown below:

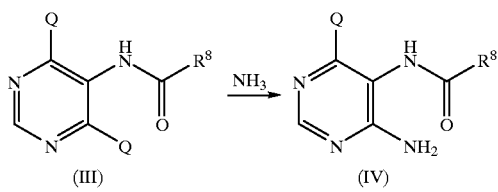

The displacement reaction occurs in the presence of ammonia, preferably aqueous ammonia in an aqueous solvent or an alcoholic solvent e.g. n-butanol. This reaction preferably occurs from about 50° C. to about 150° C., although other temperatures ranges can be used if necessary.

Step (c) of the synthetic scheme, compound (IV) is first reacted with a base e.g. phosphorous oxychloride, sodium or potassium alkoxide or other alkali metal salts (e.g. calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride), or a non-nucleophilic alternative such as saspotassium t-butoxide, to cause cyclization to the 6-halopurine intermediate. The 6-halo group is then transformed to the amine by displacement to give compound (V) of the invention, for example as shown below:

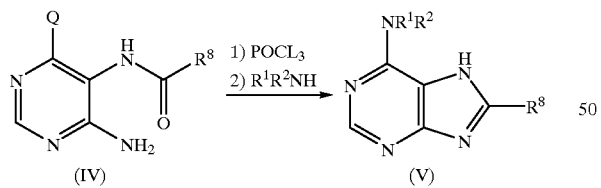

The displacement reaction occurs in the presence of ammonia or an amine, an aqueous solvent or an alcoholic solvent e.g. ethanol. This reaction preferably occurrs from about 50° C. to about 100° C., although other temperatures ranges can be used if necessary. The displacement reaction can optionally occur in a nitrogen atmosphere.

In step (d) of the reaction, compound (V) is reacted with 3-cyclopentyloxy-4-methoxybenzylhalide as shown in compound VI, wherein X is a halogen, preferably chloride, to yield compound (I) of the invention, for example as shown below:

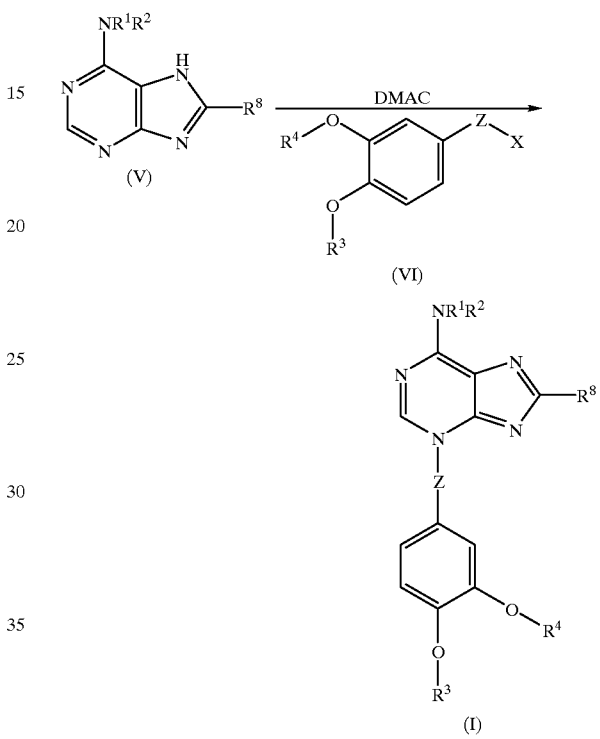

Step (d) preferably occurs in the presence of DMF or acetonitrile as solvents, although other solvents can be used. This reaction preferably occurs at at a temperature range from about 0° C. to about 200° C., preferably from about 75° C. to 175° C.

EXAMPLE 1

3-(3-Cyclopentyloxy-4-methoxybenzyl)-6-ethylamino-8-isopropyl-3H-purine

The title compound was prepared by the following synthetic pathway:

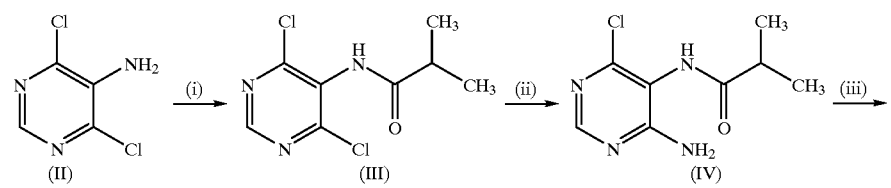

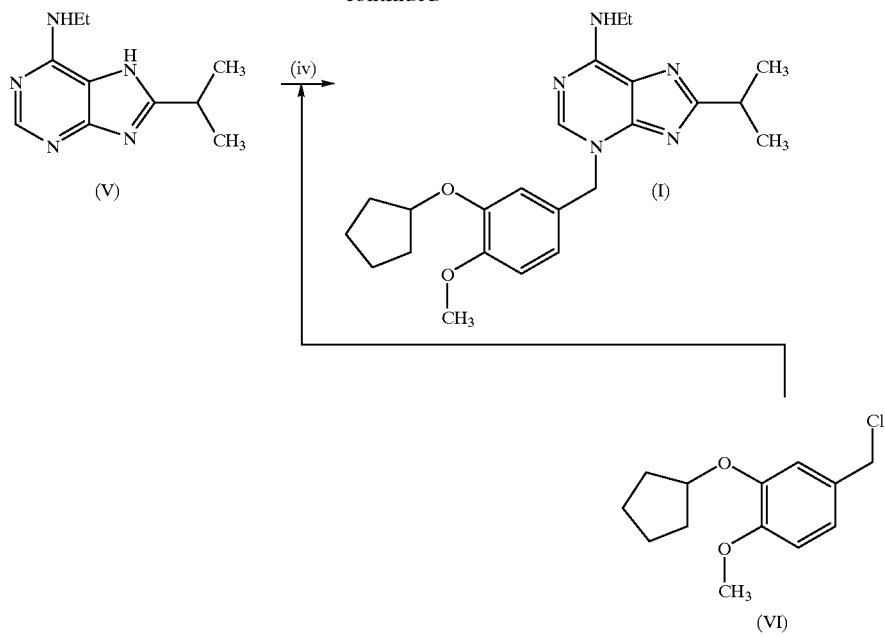

The pathway occured under the conditions set forth in Table 1 below. The pathway can occur under other suitable conditions known in the art and the particular conditions disclosed herein are not meant to be limiting.

| Step | Compound | Conditions | Yield |
|------|----------|------------|-------|
| (i) | (III) | i-PrCOCl (2.8 eq),100EC, 5 min | 89% |
| (ii) | (IV) | NH$_3$ (aq, 3 eq), n-BuOH,100EC, 24 h, | 82% |
| (iii) | (V) | POCl$_3$,100° C. EtNH$_2$,EtOH | 75% |
| (iv) | (I) | DMF, 150° C.,Compound VI | 60% |

Step (i) 5-Isobutyrylamido-4,6-dichloropyrimidine 4,6-dichloro-5-aminopyrimidine (II)(ex Aldrich), (5.65 g, 34.4 mmol) and isobutyrylchloride (10 ml, 95.55 mmol) were heated together at reflux (internal temperate 100° C., oil bath temperature 130° C.) for 10 minutes. The mixture was cooled to room temperature at which point crystallisation occurred. The mixture was triturated with ether (50 ml) to give the title compound (7.15 g, 89%) as a buff coloured crystalline solid, m.p. 161.5°–162° C. tlc (SiO$_2$, DCM:MeOH, 20:1) Rf=0.43 detection U.V.

Step (ii) 4-Amino-6chloro-5-isobutyrylamidopyrimidine 5-isobutyrylamido- 4,6-dichloropyrimidine (III)(6.0 g, 26 mmol) was dissolved in n-butanol (30 ml). Aqueous ammonia (density=0.88 g/ml) (3 ml) was added and the mixture heated to 115° C. for 24 h. Tlc (SiO$_2$, DCM:MeOH, 20:1) showed the reaction to be about 60% complete. A further 4 ml of aqueous ammonia was added and the mixture heated at reflux for 7 h. The cooled mixture was partitioned between ethyl acetate:methanol (10:1, 300 ml) and 8% aqueous sodium bicarbonate solution (300 ml). The organic phase was separated, dried (MgSO$_4$) and the solvent removed in vacuo to leave a yellow solid. Ethanol (100 ml) was added followed by ether (150 ml) and the mixture filtered, and dried overnight in-vacuo at 40° C. to give the title compound as a white solid (4.47 g, 82%) m.p. 224–225° C. Tlc, (SiO$_2$, DCM:MeOH, 20:1) Rf=0.11, detection U.V.

Step (iii) 6-Ethylamino-8-isopropyl-3H-purine

4-Amino-6-chloro-5-isobutyrylamidopyrimidine (IV)(4.0 g, 18.7 mmol) and phosphorus oxychloride (30 ml) were heated together at 110° C. for 20 h. The excess phosphorus oxychloride was removed in vacuo, and the residue triturated with ether (4H50 ml) and dried to give the intermediate chloropurine (6.3 g) m.p. 209°–211° C. The chloropurine was dissolved in ethanol (50 ml) and ethylamine (70% solution in water) (20 ml) was added and the solution heated at 70° C. under a nitrogen atmosphere for 24 h. The solvent was removed in vacuo and the residue partitioned between 10% aqueous potassium carbonate solution (100 ml) and dichloromethane:methanol (10:1, 100 ml). The organic phase was separated and the aqueous phase furthere extracted with dichloromethane-methanol (10:1, 3H100 ml). The combined organics were dried (MgSO$_4$) and evaporated to dryness in vacuo to leave a pale yellow solid (4.2 g). This was recrystallised from toluene (250 ml) to give the title compound (2.88 g, 75%) as a fluffs white crystalline solid m.p.=183–184° C. Tlc (SiO$_2$,ethyl acetate:methanol 10:1), Rf=0.59 detection U.V.

Step (iv) 6-Ethylamino-3-[(3-cyclopentyloxy-4-methoxy) benzyl]-8-isopropyl-3H-purine hydrochloride 6-Ethylamino-8-isopropyl-3H-purine (V)(7.52 g,36.65 mmol) and 3-cyclopentyloxy4-methoxybenzylchloride (10.59 g,43.98 mmol) were dissolved in acetonitrile (30 ml) in a high pressure vessel and the resulting mixture heated at 120° C. for 24 h. On cooling to room temperature a solid precipitated from the solution. The solvent was removed in vacuo, cold water (10 ml) and diethyl ether (100 ml) were added to the solid residue, the mixture stirred vigourously and then filtered. The filter cake was washed with ice-cold ethyl acetate (50 ml) and the solid obtained was oven dried in vacuo at 80° C. to give the title compound (9.51 g, 58%) as a slightly off-white solid. The combined filtrates and washings were concentrated in-vacuo, then water (5 ml) and diethyl ether (100 ml) added, and the mixture treated as before to give further title compound (0.718 g, 5%) as awhite solid, m.p.=205–207° C. Combined yield (10.23 g, 63%). Tlc, SiO$_2$ (dichloromethane: methanol, 10:1) Rf=0.49, detection U.V., Dragendorff=s reagent.

While the invention has been illustrated with respect to the production and use of particular compounds, it is apparent that variations and modifications of the invention can be made without departing from the spirit or scope of the invention.

What is claimed is:

1. A method of forming a compound having the formula (I):

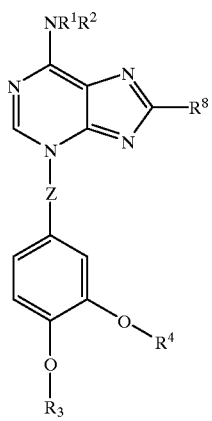

(I)

wherein:

Z is selected from the group consisting of $CH_2$, $CH_2CH_2$, $CH(CH_3)$, $CH=CH$, $C\equiv C$, $NH$, $N(C_1-C_3$ alkyl), $O$, $S$, $C(O)CH_2$ and $OCH_2$;

$R^1$ and $R^2$ are independently selected from the group consisting of hydrogen and a $C_1-C_8$ straight or branched alkyl or a $C_3-C_8$ cycloalkyl;

$R^3$ is a $C_1-C_{12}$ straight or branched alkyl;

$R^4$ is a $C_3-C_{10}$ cycloalkyl optionally substituted with OH, or a $C_3-C_{10}$ cycloalkenyl optionally substituted with OH; and $R^8$ is a $C_1-C_8$ straight or branched alkyl or a $C_3-C_8$ cycloalkyl, optionally substituted with OH; said method comprising the steps of (a) reacting a compound of the formula (II)

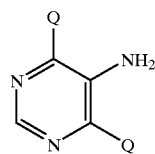

(II)

wherein Q is a halogen, with an effective amount of a compound selected from the group consisting of an acid anhydride having an $R^8C(O)$ moiety or an acid halide having an $R^8C(O)$ moiety; to form a compound of the formula (III)

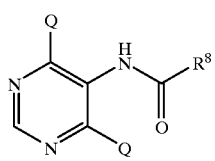

(III)

wherein Q and $R^8$ are as defined above;

(b) transforming the 6-halo group of said compound (III) to an amine by displacement with ammonia to form compound (IV)

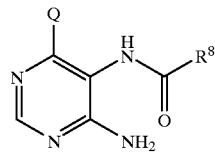

(IV)

wherein Q and $R^8$ are as defined above;

(c) reacting said compound (IV) with a base to cause cyclization to a 6-halo intermediate, said 6-halo group is then transformed to an amine by displacement with an amine group of the formula $NR_1R_2$, wherein $R_1R_2$ are as defined above, to form compound (V)

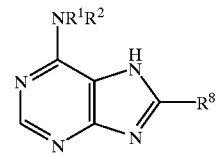

(V)

wherein $R^1$, $R^2$ and $R^8$ are as defined above;

(d) reacting said compound (V) with an effective amount of compound (VI)

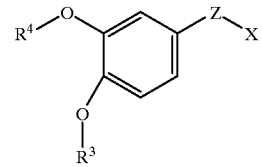

(VI)

where $R^3$ and $R^4$ are as defined above and X is a halogen; to form the compound of formula (I).

2. The method of claim 1 wherein $R^4$ is cyclopentyl.
3. The method of claim 2 wherein $R^3$ is methyl.
4. The method of claim 3 where Z is $CH_2$.
5. The method of claim 1 wherein Q is chloride.
6. The method of claim 1, wherein said acid chloride isobutyrylchloride.
7. The method of claim 1, wherein said base is phosphorous oxychloride.
8. The method of claim 1, wherein said step (b) occurs in an alcoholic or aqueous solvent.
9. The method of claim 8, wherein said alcoholic solvent is n-butanol.
10. The method of claim 1, wherein said step (d) occurs in N,N-dimethylformamide.
11. The method of claim 1 wherein X is chloride.
12. The method of claim 1 wherein said compound of formula I is 3-(3-cyclopentyloxy-4-methoxybentyl)-6-ethylamino-8-isopropyl-3H-purine.

* * * * *